(12) United States Patent
Betzold et al.

(10) Patent No.: US 7,881,793 B2
(45) Date of Patent: Feb. 1, 2011

(54) SYSTEM AND METHOD FOR VENTRICULAR PACING WITH PROGRESSIVE CONDUCTION CHECK INTERVAL

(75) Inventors: Robert A. Betzold, Fridley, MN (US); David A. Casavant, Reading, MA (US); Paul A. Belk, Maple Grove, MN (US); Thomas J. Mullen, Andover, MN (US); John C. Stroebel, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 991 days.

(21) Appl. No.: 11/096,436

(22) Filed: Mar. 31, 2005

(65) Prior Publication Data

US 2005/0177197 A1    Aug. 11, 2005

(51) Int. Cl.
*A61N 1/368* (2006.01)
(52) U.S. Cl. .................................................. 607/27
(58) Field of Classification Search ............... 600/373, 600/374, 377, 393, 508, 509; 607/4, 6, 7, 607/9, 11, 16, 17, 27, 28, 116, 119, 122, 607/123
See application file for complete search history.

(56) References Cited

U.S. PATENT DOCUMENTS

| | | | |
|---|---|---|---|
| 3,057,356 A | 10/1962 | Greatbatch | |
| 3,253,596 A | 5/1966 | Keller | |
| 3,478,746 A | 11/1969 | Breatbatch | |
| 3,595,242 A | 7/1971 | Berkovits | |
| 3,648,707 A | 3/1972 | Greatbatch | |
| 3,747,604 A | 7/1973 | Berkovits | |
| 4,312,355 A | 1/1982 | Funke | |
| 4,428,378 A | 1/1984 | Anderson et al. | |
| 4,476,868 A | 10/1984 | Thompson | |
| 4,523,593 A | 6/1985 | Rueter et al. | |
| 4,856,523 A | 8/1989 | Sholder et al. | |
| 4,890,617 A | 1/1990 | Markowitz et al. | |
| 4,932,046 A | 6/1990 | Katz et al. | |
| 5,052,388 A | 10/1991 | Sivula et al. | |
| 5,318,594 A | 6/1994 | Limousin et al. | |
| 5,345,362 A | 9/1994 | Winkler | |

(Continued)

FOREIGN PATENT DOCUMENTS

EP     0 448 193     9/1991

(Continued)

OTHER PUBLICATIONS

"Intrinsic™/Intrinsic™ 30, 7288/7287 Reference Manual", May 24, 2004, 9 pgs.

*Primary Examiner*—Carl H Layno
*Assistant Examiner*—Frances P Oropeza
(74) *Attorney, Agent, or Firm*—Stephen W. Bauer; Reed A. Duthler

(57) ABSTRACT

A pacing protocol is provided that reduces or minimizes ventricular pacing in favor of intrinsic conduction. When operating in a mode that provides ventricular pacing, a series of conduction checks are performed to determine if intrinsic conduction has returned. These conduction checks occur according to a predetermined pattern that general includes longer intervals between subsequent attempts. A maximum interval is provided such that conduction checks are not repeated sequentially at the same time of day when at this maximum interval.

21 Claims, 11 Drawing Sheets

U.S. PATENT DOCUMENTS

| | | |
|---|---|---|
| 5,388,586 A | 2/1995 | Lee et al. |
| 5,643,326 A | 7/1997 | Weiner et al. |
| 5,814,077 A | 9/1998 | Sholder et al. |
| 5,861,007 A | 1/1999 | Hess et al. |
| 5,873,895 A * | 2/1999 | Sholder et al. ......... 607/9 |
| 5,954,755 A | 9/1999 | Casavant |
| 6,122,546 A | 9/2000 | Sholder et al. |
| 6,169,918 B1 | 1/2001 | Haefner et al. |
| 6,256,541 B1 | 7/2001 | Heil et al. |
| 6,397,105 B1 | 5/2002 | Bouhour et al. |
| 6,772,005 B2 | 8/2004 | Casavant et al. |
| 7,130,683 B2 * | 10/2006 | Casavant et al. ......... 607/9 |

FOREIGN PATENT DOCUMENTS

| | | |
|---|---|---|
| EP | 0 830 877 | 3/1998 |
| WO | WO95/32758 | 12/1995 |
| WO | WO02/051499 | 7/2002 |

* cited by examiner

SYSTEM AND METHOD FOR VENTRICULAR PACING WITH PROGRESSIVE CONDUCTION CHECK INTERVAL

CROSS-REFERENCE TO RELATED APPLICATIONS

This patent application is related to U.S. patent application Ser. No. 10/755,454, filed on Jan. 12, 2004, entitled "PREFERRED ADI/R: A PERMANENT PACING MODE TO ELIMINATE VENTRICULAR PACING WHILE MAINTAINING BACKUP SUPPORT", now U.S. Pat. No. 7,218,965, which is a continuation of prior U.S. patent application Ser. No. 10/246,816, filed Sep. 17, 2002, entitled "PREFERRED ADI/R: A PERMANENT PACING MODE TO ELIMINATE VENTRICULAR PACING WHILE MAINTAINING BACKUP SUPPORT", now U.S. Pat. No. 7,130,683, which is a continuation-in-part of Ser. No. 09/746,571, filed Dec. 21, 2000, entitled "PREFERRED ADI/R: A PERMANENT PACING MODE TO ELIMINATE VENTRICULAR PACING WHILE MAINTAINING BACKUP SUPPORT", now U.S. Pat. No. 6,772,005 all of which are herein incorporated by reference in their entirety. The present application is also related to U.S. patent application Ser. No. 10/814,692, filed on Mar. 31, 2004 and entitled "FULLY INHIBITED DUAL CHAMBER PACING MODE", now U.S. Pat. No. 7,254,441 and U.S. patent application Ser. No. 10/850,666, filed on May 21, 2004 and entitled "VENTRICULAR EVENT FILTERING FOR AN IMPLANTABLE MEDICAL DEVICE", now U.S. Pat. No. 7,245,966 both of which are continuations-in-part of U.S. patent application Ser. No. 10/246,816, filed Sep. 17, 2002, entitled "PREFERRED ADI/R: A PERMANENT PACING MODE TO ELIMINATE VENTRICULAR PACING WHILE MAINTAINING BACKUP SUPPORT", now U.S. Pat. No. 7,130,683, which is a continuation-in-part of Ser. No. 09/746,571, filed Dec. 21, 2000, entitled "PREFERRED ADI/R: A PERMANENT PACING MODE TO ELIMINATE VENTRICULAR PACING WHILE MAINTAINING BACKUP SUPPORT", now U.S. Pat. No. 6,772,005 all of which are herein incorporated by reference in their entirety.

FIELD OF THE INVENTION

The present invention generally relates to implantable medical devices and more specifically to implantable medical device capable of cardiac pacing.

BACKGROUND OF THE INVENTION

In providing cardiac pacing, there is a preference to promote intrinsic conduction and intrinsic depolarization of the ventricles and to reduce or minimize ventricular pacing. Various protocols have been provided to promote intrinsic conduction with varying degrees of success. For example, in some modes a programmed AV (atrial-ventricular) delay is extended and if underlying conduction is present, the sensed ventricular event will inhibit a subsequent ventricular pace. While useful, such AV extensions are limited in that the maximum intervals available must remain consistent with the capabilities of traditional pacing modalities. That is, such an AV interval may be defined within a DDD or DDDR mode, for example. For any given cardiac cycle, a ventricular pace will be delivered at the end of the AV delay absent sensed ventricular activity. Therefore, there is a maximum AV delay, beyond which a ventricular pace may not be safely delivered in a given cardiac cycle.

According the protocols of the present invention and as defined in greater detail in the above incorporated applications, modes are provided that permit an entire cardiac cycle to pass without ventricular pacing, even in the absence of a sensed ventricular event. This provides the maximum opportunity during a given cardiac cycle for intrinsic conduction to occur. Such protocols may be referred to collectively as "Managed Ventricular Pacing™" (MVP™) or a "ventricular pacing protocol" (VPP).

In practice, a given patient may perform quite well with a given VPP that provides no ventricular pacing; that is, effectively acting in an AAIR, AAI, ADI, or ADIR mode so long as intrinsic conduction is either always present or lacking so infrequently as to be tolerated by the VPP. Other patients, for example those with complete heart block, may be pacemaker dependant and require constant ventricular pacing. In such instances, the VPP does not have any opportunity to reduce ventricular pacing, as that pacing is critical for survival. Finally, there are patients who fluctuate between the two extremes. These patients will sometimes require ventricular pacing and at other time will exhibit intrinsic conduction either at normal or prolonged intervals.

With the patients who fluctuate, the VPP will operate in an atrial based pacing mode when permissible and operate in a dual chamber pacing mode when ventricular pacing is required. It should be appreciated that the present description is provided as an overview and is not meant to be limiting; that is, in some instances the VPP will mode switch from one mode to another whereas in other instances the VPP includes a single mode that effectuates both the atrial based and dual chamber based functionality. Thus, for purposes of description an indication of an atrial based or dual chamber based mode (with reference to a VPP) is indicative of the functionality imparted and includes either an actual mode status/switch or the functional status of a VPP using a single mode inclusive of both aspects. Furthermore, atrial based pacing mode simply means that ventricular pacing is generally not provided (for a given cycle) and a dual chamber mode means that ventricular pacing is available. Thus, these distinctions, as used herein do not preclude triple chamber pacing, four chamber pacing, or other multi-site pacing arrangements.

As indicated, various patients will fluctuate between requiring and not requiring ventricular pacing. As such, a change to a dual chamber based pacing mode is generally not expected to be permanent. That is, the device will periodically perform conduction checks to determine if intrinsic conduction is present and therefore facilitate a return to an atrial based pacing mode.

DETAILED DESCRIPTION OF THE DRAWINGS

Figure 1:
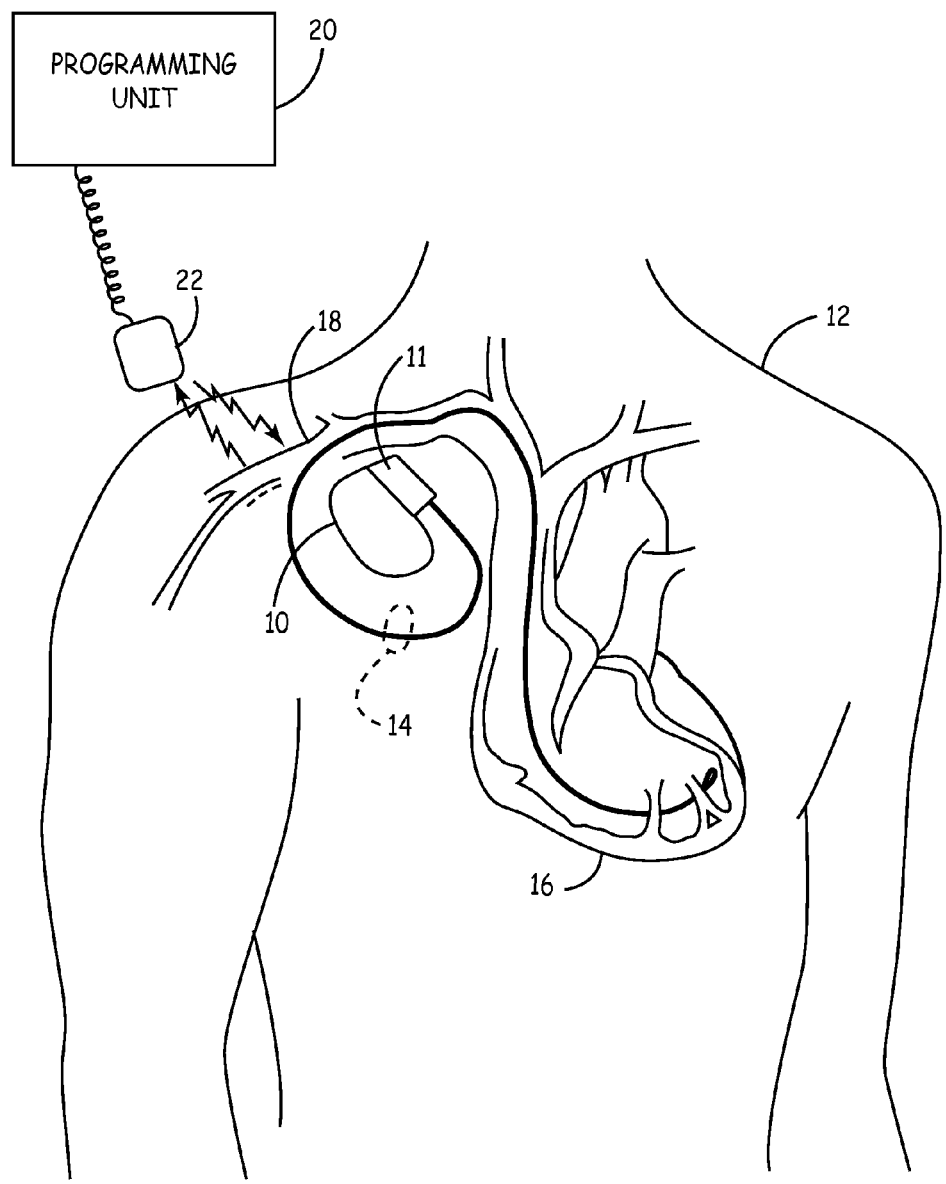
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable medical device ("IMD") 10, such as a pacemaker that has been implanted in a patient 12. It should be appreciated that the IMD 10 may be pacemaker or may also include cardioversion and/or defibrillation capabilities such as with an implantable cardioverter/defibrillator (ICD). The IMD 10 is housed within a hermetically sealed, biologically inert outer casing, which may itself be conductive so as to serve as an indifferent electrode in a pacing/sensing circuit. One or more pacemaker leads, collectively identified with reference numeral 14 in FIG. 1 are electrically coupled to the IMD 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

The IMD 10 is illustrated in FIG. 1 as being implanted in a "pocket" typically defined below the pectoral muscle, with leads 14 extending through the vasculature into the heart. IMD 10 may alternatively be embodied in a subcutaneously implanted device either with electrodes that are remote from the heart 16 or including lead extending to an interior or exterior portion of the heart 16.

Figure 2:
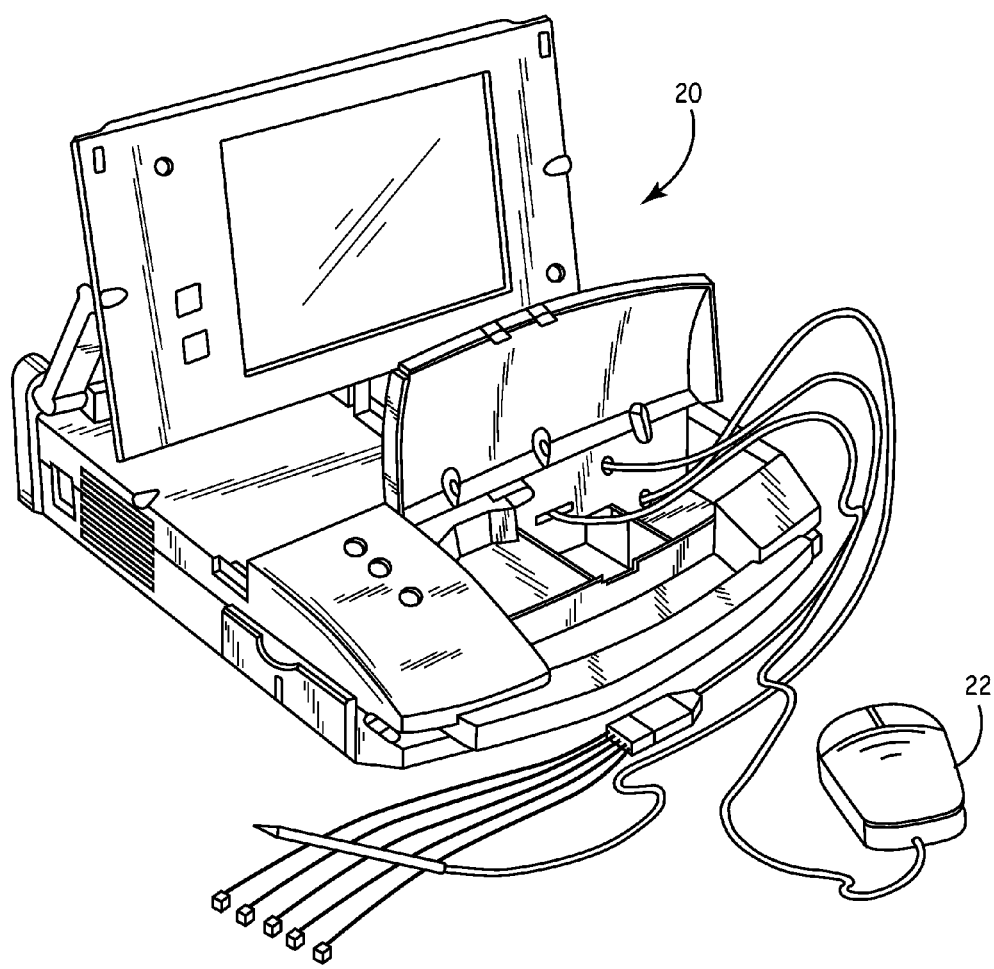
FIG. 2 is a perspective view of the external programming unit of FIG. 1.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between IMD 10 and programmer 20. In many known implantable device systems, a programming head such as that depicted in FIG. 1 is positioned proximate the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art. Alternatively or additionally, communication with programming unit 20 occurs over a greater distance through RF transmission with the incorporation of the appropriate transceiver in the IMD 10. FIG. 2 is a perspective view of one embodiment of programming unit 20 in accordance with the presently disclosed invention.

Figure 3:
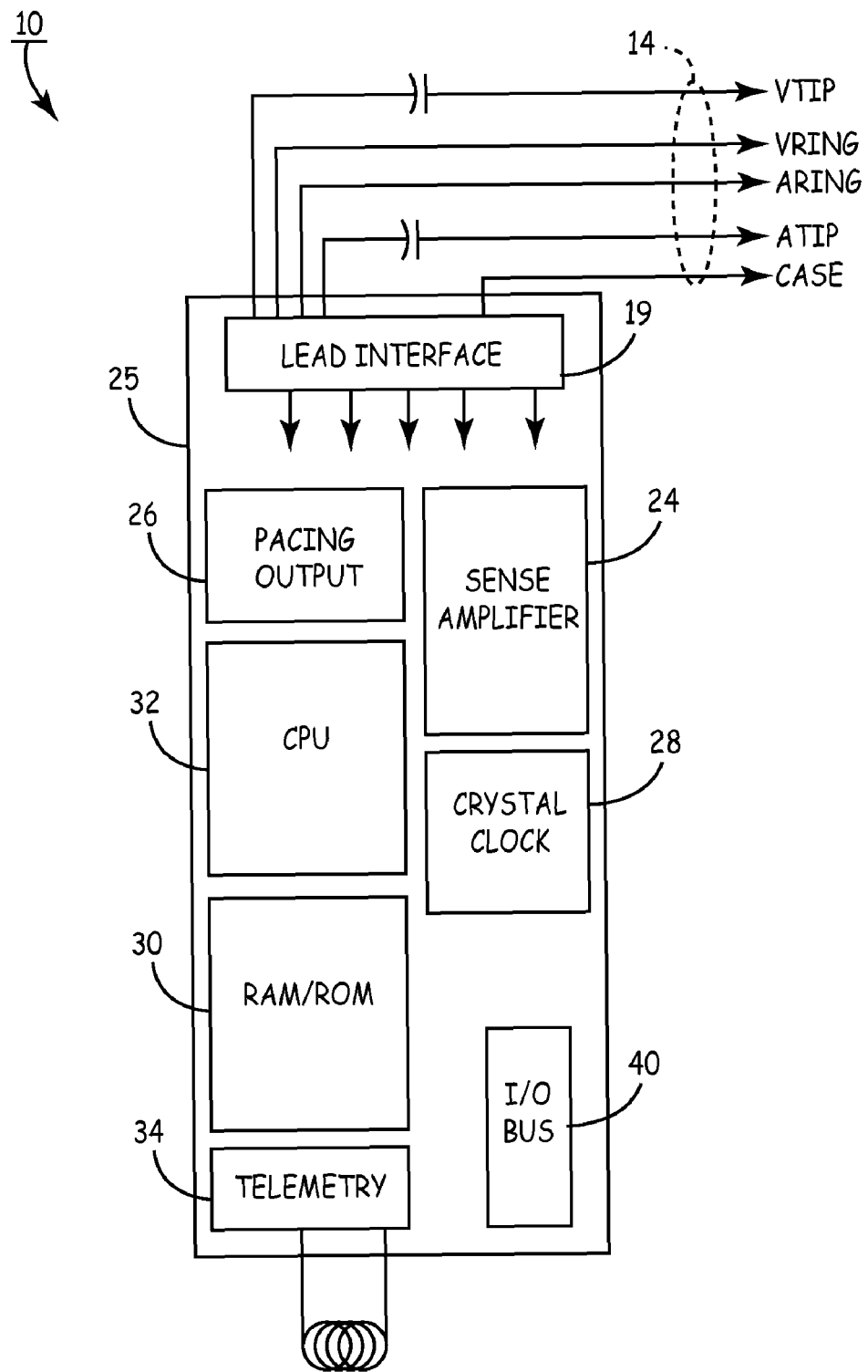
FIG. 3 is a block diagram of the implanted device from FIG. 1.

FIG. 3 is a block diagram of one embodiment of the electronic circuitry that makes up pulse generator in IMD 10. A primary stimulation control circuit 25 controls the IMD's pacing and sensing functions. For example, stimulation control circuit 25 in FIG. 3 includes sense amplifier circuitry 24, stimulating pulse output circuitry 26, a crystal clock 28, a random-access memory and read-only memory (RAM/ROM) unit 30, an input/output bus 40, and a central processing unit (CPU) 32. IMD 10 also includes internal communication circuit 34 so that it is capable communicating with external programmer/control unit 20.

With continued reference to FIG. 3, IMD 10 is coupled at connector block assembly 11 to one or more leads 14 which, when implanted, extend transvenously between the implant site and the patient's heart 16. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of IMD 10.

Figure 4:
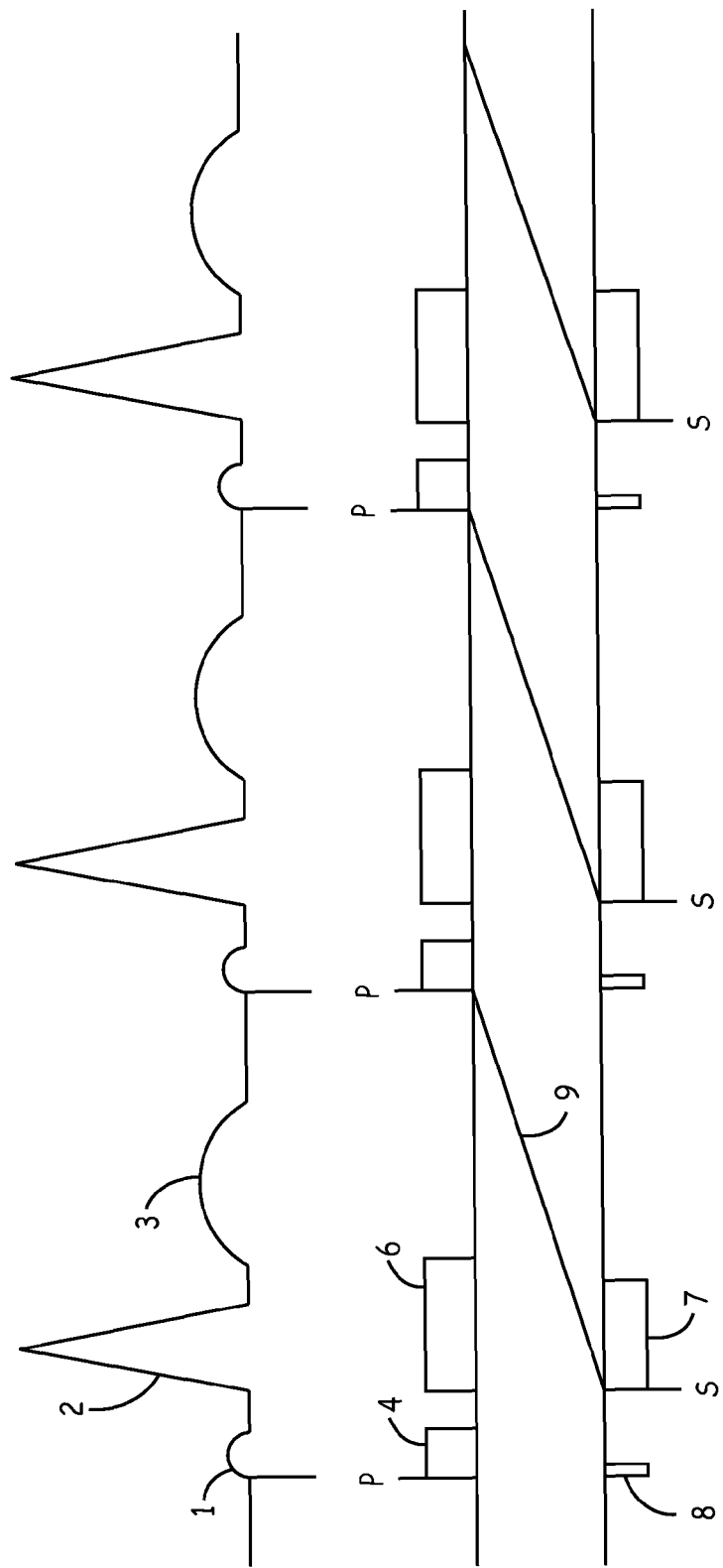
FIG. 4 is a ladder diagram of the ADI/R operation.

FIG. 4 is a ladder diagram illustrating IMD operation in an ADI/R mode with a Marker Channel® Diagram. With the help of the NBG Code, one familiar with the state of the art will be able to discern that the letter in the first position (A) means that the pacemaker (or other implanted device) will pace the atrium in the absence of an atrial sensed event. The second letter (D) implies that the pacemaker will sense in dual chambers, that is, both the atrial and ventricular chambers. The third letter (I) means that, upon sensing in either chamber, pacing will be inhibited in that specific chamber. The final letter, R, implies that the device may be rate responsive, that is, altering the atrial rate in response to an artificial sensor, such as a Piezo-electrical crystal, accelerometer, minute ventilation, etc.

The operation in the ADI/R mode is depicted in the ladder diagram as follows. Atrial paced (or sensed) event 1 initiates a non-programmable, auto-adjusting (e.g., 100-150 millisecond) blanking period 4, followed by auto-adjusting atrial sensitivity (not shown). Sensing circuitry (see FIG. 3) determines if and when ventricular sensed event 2 has occurred. If detected, timing circuitry (see FIG. 3) initiates VA interval 9. Other timing, blanking periods, and refractory periods serve the following purposes. A programmable ventricular blanking period 8 prevents sensing of atrial pace 1 on the ventricular channel, sometimes termed "crosstalk." Ventricular sensed event 2 starts a 120 millisecond post ventricular atrial blanking (PVAB) period 6, followed by auto-adjusting atrial sensitivity. PVAB 6 serves the purpose of preventing sensing of the R-wave or T-wave on the atrial channel, termed "far-field R-wave sensing." Ventricular sensed event 2 also starts 100 millisecond ventricular blanking 7 followed by auto-adjusting ventricular sensitivity. This period serves the purpose of preventing sensing of the ventricular output pulse or the ventricular depolarization itself. Repolarization, or T-wave 3, follows R-wave 2. Ventricular event 2 detected by sensing circuitry (see FIG. 3) sends signal to timing circuitry to start VA interval 9, leading to the next atrial pacing cycle.

Figure 5:
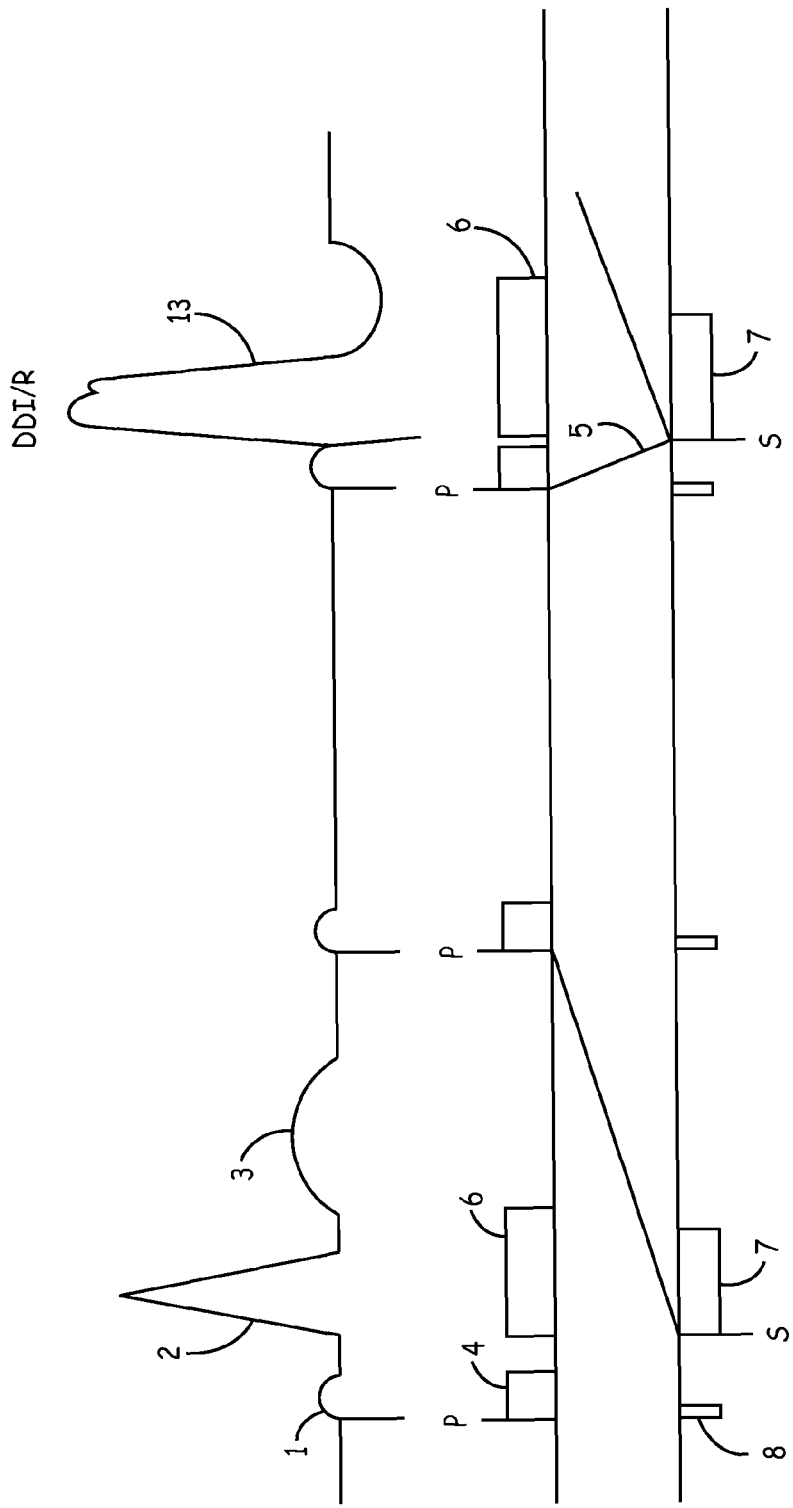
FIG. 5 is a ladder diagram of the committed DDD/R operation in the event that the patient develops transient AV block.

Taking into account that this mode would be used primarily with Sick Sinus patients who have full or some degree of intact AV conduction, this type of operation as depicted for the ADI/R mode is something the clinician or physician would expect to occur. In the presence of intact AV conduction, even if it is prolonged, the pacemaker will maintain the ADI/R operation/mode. Sensed ventricular events would occur in the vast majority of cardiac cycles (that is, PQRST). FIG. 5 teaches what will occur should the patient develop transient AV block for one or a few cardiac cycles.

FIG. 5 is a ladder diagram of the committed DDI/R operation in the event that the patient develops transient AV block. The purpose of the committed DDI/R operation is to maintain ventricular support in the presence of AV block. Briefly stated, the implanted device mode switches from the preferred ADI/R to the committed DDI/R for one cycle.

The timing of the Committed DDI/R is as follows. In the DDI/R mode (third pacing cycle, labeled DDI/R), AV interval 5 is set to a short 80 milliseconds, following the Paced P-wave due to the absence of any sensed ventricular event between the second and third atrial paced events. The purpose of this short AV interval 5 is to suppress competition between ventricular pacing pulse culminating in paced R-wave 13 and any potential intrinsic R-wave with a delayed conduction from the previous paced atrial event. Assuming the presence of such an intrinsic R-wave, the timing of the ventricular output pulse would normally result in a ventricular pacing pulse falling into the absolute refractory period of the intrinsic, conducted R-wave, resulting in a psuedo-fusion beat (not shown). This operation is intended to prevent the onset of a ventricular tachycardia, should the ventricular pacing pulse fall into the relative refractory period of the ventricle, commonly called "pacing on T" phenomenon.

Continuing with the timing in FIG. 5, paced R-wave 13 starts a 120 millisecond ventricular blanking period 7, followed by auto adjusting ventricular sensitivity (not shown). Paced R-wave 13 also starts a 120 millisecond PVAB 6 followed by auto adjusting atrial sensitivity (not shown). Assuming the transient AV block self-corrects and a sensed R-wave is detected, the preferred ADI/R resumes with the next paced or sensed P-wave, as is depicted in FIG. 4.

Figure 6:
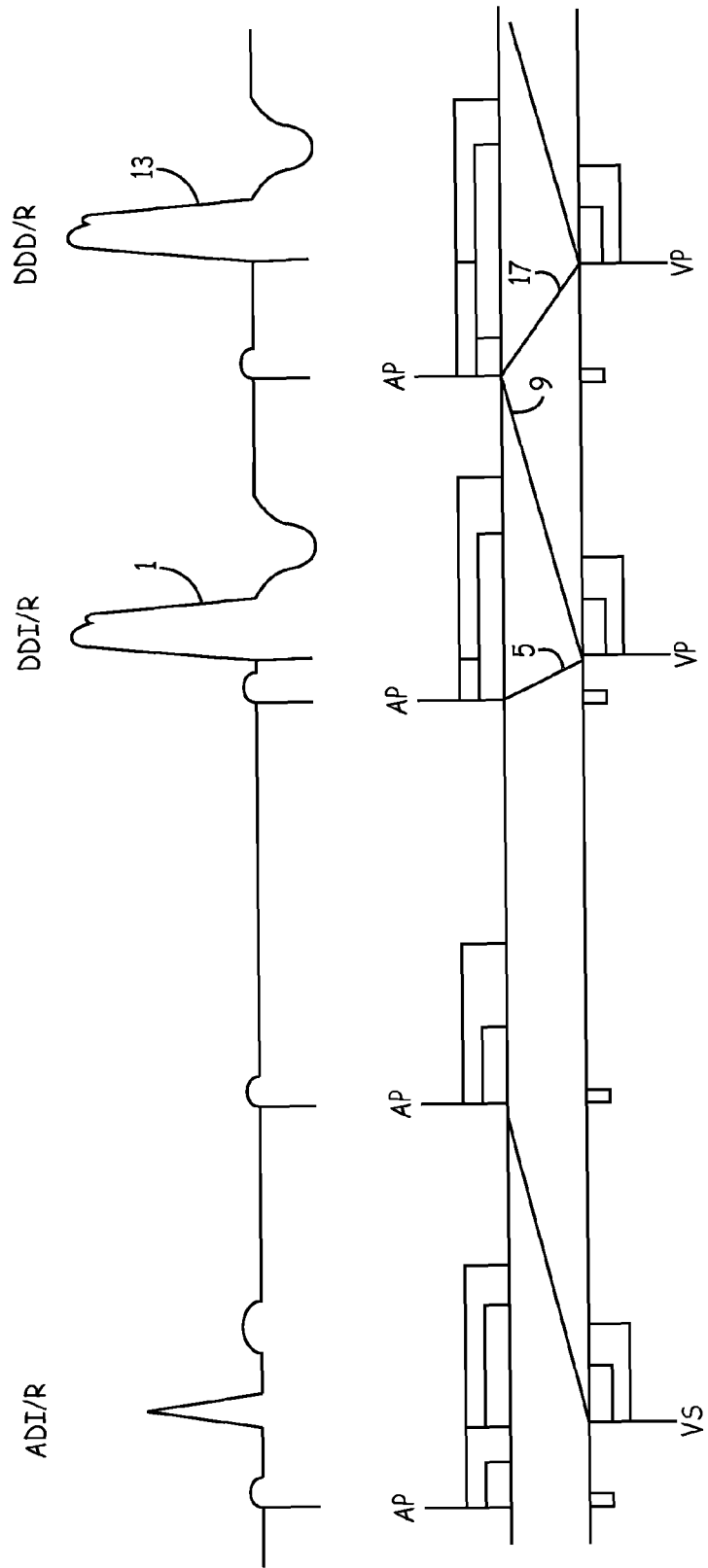
FIG. 6 is a ladder diagram that depicts the pacing operation in the event that the patient develops AV block that persists for more than one cycle.
Figure 7:
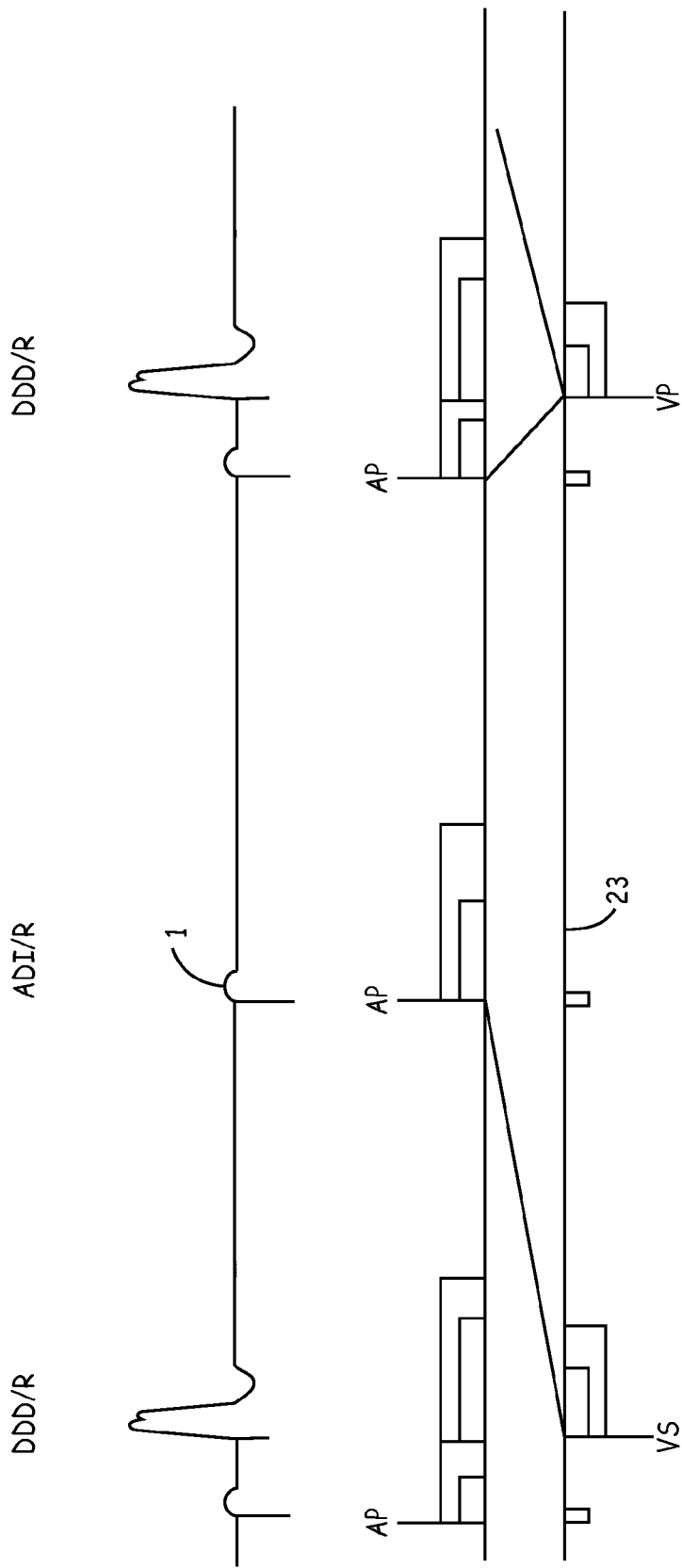
FIG. 7 is a ladder diagram that depicts a periodic attempt to restore the ADI/R operation during sustained DDD/R operation.

FIG. 6 is a ladder diagram that depicts the pacing operation in one embodiment in the event that the patient develops AV block that persists for more than one cycle. Note that according to the preferred embodiment of the present invention, a single missed beat (i.e., no Vs) will not by itself cause a mode switch, particularly if relatively reliable AV conduction is present. Following the one-cycle mode switch to DDI/R, VA interval 9 times out, resulting in atrial paced event 1. A very long (e.g. 400 millisecond or up to 65% of the sensor-indicated AV interval) 17 is used in an attempt to promote AV conduction. If, however, AV interval 17 is not interrupted by a sensed, intrinsic R-wave, as is depicted in the first cycle (labeled ADI/R), the pacemaker immediately switches to the DDD/R mode. In the event that a sensed, intrinsic R-wave does occur, the device would revert to the ADI/R operation (not shown). The DDD/R operation, with the programmed AV interval, will be sustained until a sensed, intrinsic R-wave is detected. Periodic attempts to force restoration of the ADI/R operation are performed (as depicted in FIG. 7). Mode switching to the DDI/R mode will occur in the event that an atrial tachycardia is detected (see FIG. 8).

FIG. 7 is a ladder diagram that depicts a periodic attempt to restore the ADI/R operation during sustained DDD/R operation. As mentioned, the DDD/R mode may become the sustained mode of operation in the event that the patient develops a prolonged AV block, such as might occur with rate-dependent AV block. In such cases, the device may be programmed to revert to ADI/R 1 after a programmable number of DDD/R cycles. Then, the device looks for a ventricular sensed event, e.g., at 23 following atrial pace 1. In the event that a sensed, intrinsic R-wave is detected, the ADI/R operation is immediately resumed. In the absence of a ventricular sensed event, the device continues to operate in the DDD/R mode, as indicated in the third cycle of FIG. 7.

Figure 8:
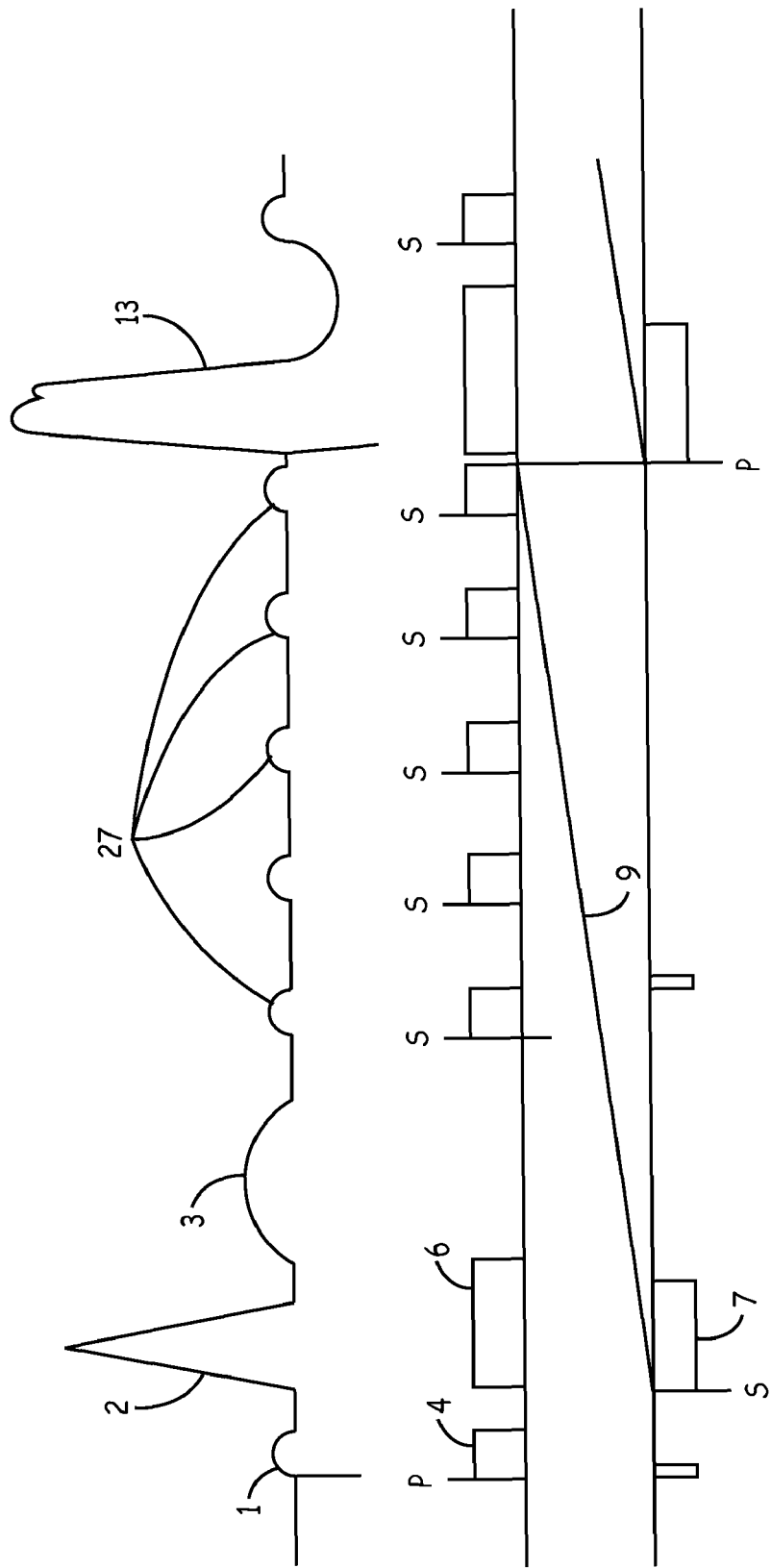
FIG. 8 is a ladder diagram of the pacing operation in the event that the patient develops an atrial tachycardia.

FIG. 8 is a ladder diagram of the pacing operation in the event that the patient develops an atrial tachycardia. A sick sinus patient often has episodes of atrial tachycardia, atrial flutter, or atrial fibrillation. During these episodes, the pacing operation must be such that the ventricular pacing rate will neither be synchronized to the fast atrial rate nor so slow as to cause symptoms.

In FIG. 5 it was noted that the device, while operating in the ADI/R mode, can switch to the DDI/R mode. The DDI/R mode is well suited for pacing in the presence of an atrial tachycardia because it will not allow ventricular synchronization to a fast atrial rate nor will it allow the ventricular pacing rate to go below the programmed lower rate. Therefore, when an atrial tachycardia does occur, as shown in FIG. 8, fast atrial sensed events 27 without a conducted ventricular event have no effect on ventricular timing 9. Since there is no ventricular event, the operation immediately switches to the DDI/R mode. In the presence of an atrial tachycardia, the V-V interval 9 times out so that paced R-wave 13 will occur at the faster of the programmed lower rate or sensor-indicated rate in the DDI/R mode. The operation depicted in FIG. 8 will continue so long as the atrial tachycardia persists. Upon termination of the atrial tachycardia, the preferred ADI/R will resume as shown in FIG. 4 or 7, depending on how the heart recovers from the atrial tachyarrhythmia. If the atrial tachyarrhythmia terminates abruptly, the prompt restoration of the ADI/R mode takes place (see FIG. 4). If, however, the atrial tachyarrhythmia "cools down" slowly, there may be a period of DDD/R pacing with periodic attempts to restore ADI/R pacing as shown in FIG. 7.

Figure 9:
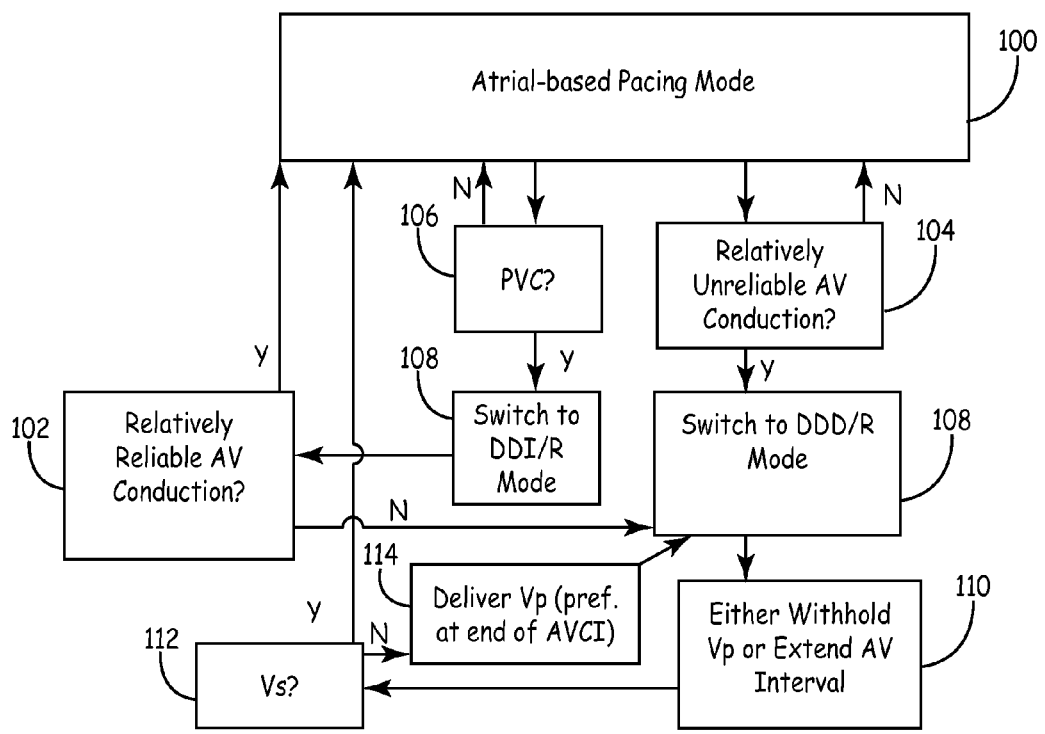
FIG. 9 is a flow chart illustrating one embodiment of a mode supervisor according to the present invention.

With general reference to FIG. 9, the ventricular pacing protocols include one or more of the following aspects. A mode supervisor (100) is included and controls a wide range of operations related to mode changes. The mode supervisor (100) may be a hardware, software, or firmware based module. One aspect of the mode supervisor (100) monitoring a patient's atrial-ventricular status and intervening when necessary by invoking sustained mode-switches (108) to conventional modes of pacing (i.e. DDD/R and DDI/R). The mode supervisor (100), in one embodiment, defines unreliable AV conduction according to a Wenckebach pattern with definition of a critical AV conduction acceptance ratio to discriminate between tolerable (or "relatively reliable") AV conduction states (100) from intolerable (or "relatively unreliable") AV conduction (104) states. For instance, an AV conduction acceptance ratio of 4:3 allows preferred ADI/R operation to persist as long as there are at least three ventricular events for every four physiologic atrial events. Should AV conduction falter such that the ratio of A to V events falls below the pre-defined acceptance ratio, a sustained switch (108) to conventional DDD/R pacing will occur. Atrial events classified as non-physiologic (i.e. within the ARP) are not accounted for in the calculation of the A:V ratio. Thereby, inappropriate mode-switches (108) to DDD/R are avoided in the presence of frequent non-conducted premature atrial contractions (PAC) (106).

Upon invoking DDD/R pacing (108) in the presence of unreliable AV conduction, the mode supervisor (100) immediately assumes the role of striving to restore ADI/R pacing (110). Since it is known that AV conduction disease typically progresses gradually with brief manifestations of high degree block expected in the early stages of disease progression, the mode supervisor (100) will attempt to restore ADI/R operation following only a brief episode of new onset DDD/R pacing. Accordingly, the first reattempt to reveal intact AV conduction and to restore ADI/R pacing will occur only after a short period of time (e.g., one minute) of DDD/R pacing. Should ADI/R restoration fail, reattempts will occur at 2, 4, 8, 16 and 32 minutes and subsequently at 1, 2, 4, 8, 12 and 16 hours. Of course, other timing sequences may be used, both periodic and aperiodic (as well as local and remote clinician- or patient-activated atrial-based pacing initiation).

As indicated, the IMD 10 will periodically attempt to return to an atrial based pacing mode. Similarly, as discussed below, frequent mode switching may lead to a sustained switch to a dual chamber mode with subsequent attempts to return to the atrial based mode made at given intervals. This process of deliberately attempting to return to an atrial based mode from a dual chamber based mode will be referred to herein generally as a "conduction check" or "conduction checking." As noted in the embodiment above, the delay between each conduction check is progressive and increasing. In the example provided, attempts are made at 2, 4, 8, 16 and 32 minutes and then at 1, 2, 4, 8, 12 and 16-hour intervals. The particular values chosen and the number of attempts made with a given interval before moving to a larger interval can be varied. For example, a pattern such as 1, 1, 2, 2, 4, 4, 8, 8, 8, etc. may be utilized.

In one embodiment of the present invention, the conduction check timing interval or progression is chosen to be non-anticipatory to the patient and/or to avoid circadian repetition. In general, the occasional absence of a ventricular depolarization will be unnoticed by the patient. However, frequent skipped beats might be perceptible. In such a case, if a conduction check were performed every minute or every three minutes (e.g., a relatively short interval) and the skipped beat was perceived by the patient, then the effects either physiological or psychological on the part of the patient may result in an unsuccessful conduction check. For example, the patient may become tense or stressed in anticipation, resulting in an elevated heart rate, and under the right circumstances, this may hinder the emergence of the underlying intrinsic conduction. Thus, the pattern is staggered and set at increasing intervals such the patient does not anticipate the conduction checks. Simply for illustration, perhaps the patient perceives the conduction check at two minutes and tenses. Four minutes later, the patient could still be tense; eight or sixteen minutes later, the patient has most likely lost focus on the issue and is relaxed making for a more effective conduction check.

Assuming the conduction checks fail as progressively attempted, a maximum value is reached. In the above example, this value is 16 hours. That is, a conduction check is performed once every 16 hours. This value avoids circadian repetition. This simply means that the conduction check will not occur at the same time of day on a day-to-day basis. Consider a hypothetical patient that develops transient block that lasts sufficiently long to cause the conduction check interval to reach a maximum. Subsequently, intrinsic conduction resumes (or would in the absence of pacing), but block occurs during periods of sleep. If the maximum interval were 24 hours, the conduction check could continuously be attempted when the patient is asleep and thus, will fail. Such a situation will forgo the benefits of reduced ventricular pacing during the waking hours. By utilizing a maximum value of, e.g., 16 hours, the conduction check occurs at different times of the day and avoids the above-described scenario. Of course, intervals of other than 16 hours may be chosen to accomplish this as well. However, if the chosen interval is relatively close to 24 hours (e.g., 23 hours), then the conduction check could occur during the same circadian interval (e.g., night or sleeping hours) for many consecutive days.

Thus, there are several factors in determining the timing of the conduction check progression. Initially, the checks are conducted frequently and over short durations. Assuming they fail, the intervals become longer until that maximum value is reached. This maximum value should be long enough such that it is not wasteful of resources; short enough such that patient benefit may be achieved relatively quickly if intrinsic conduction returns; staggered to avoid circadian repetition; and optionally selected such that the staggering avoids prolonged repetition in circadian cycles (e.g., the 23 hour example).

Figure 10:
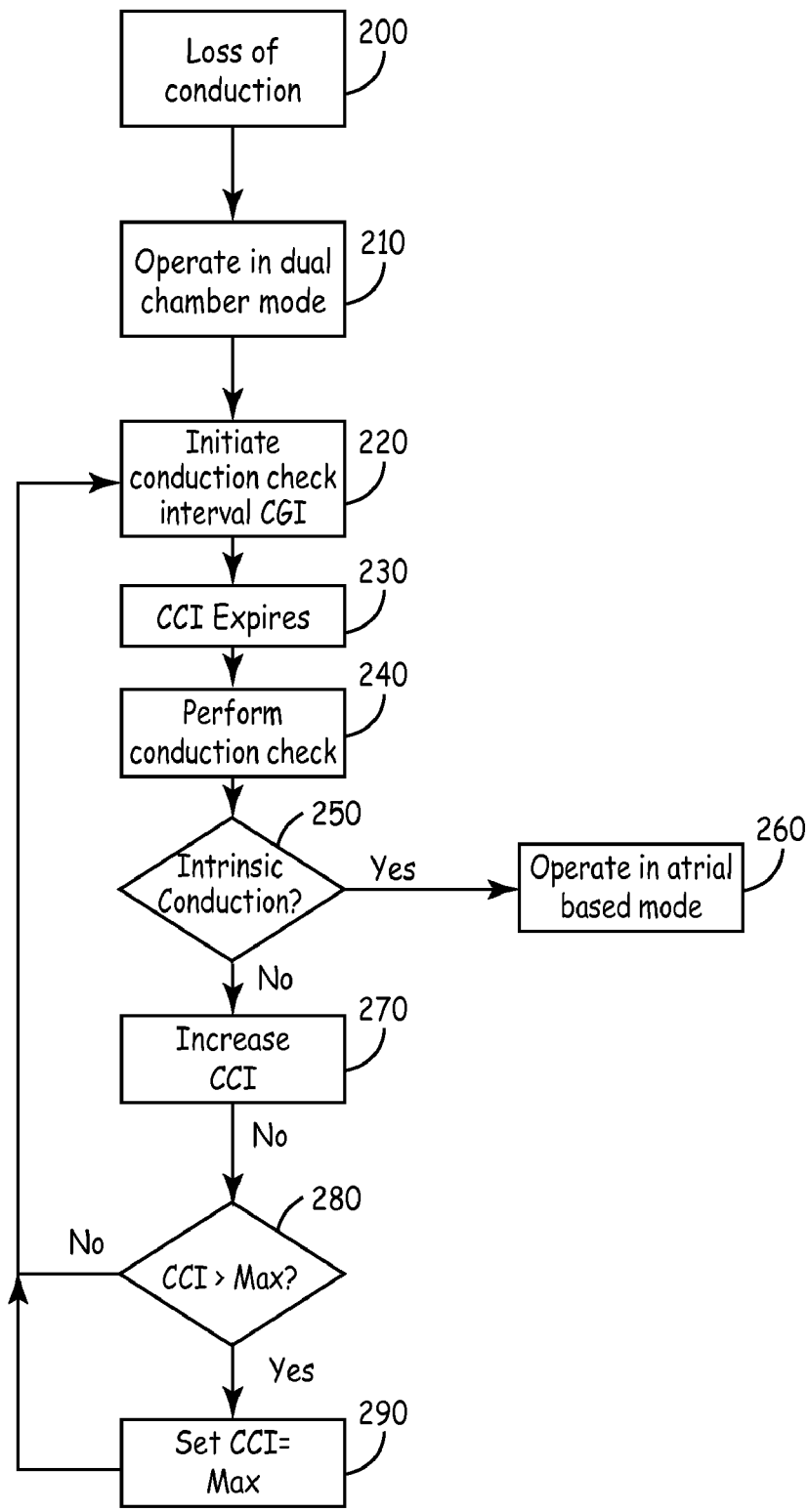
FIG. 10 is a flowchart illustrating a process for performing conduction checks.

FIG. 10 is a flowchart illustrating a process for performing conduction checks. While operating in an atrial based pacing mode according to a ventricular pacing protocol as described, the patient has a loss (200) of intrinsic conduction. While any given protocol may take several cycles to do so, after a period of time, the device will generally operate (210) in a dual chamber-pacing mode (e.g., DDD/R). The IMD 10 initiates (220) a conduction check interval (CCI) that is a timer, count of pacing cycles, or similar mechanism used to indicate when the device should attempt a conduction check. At the expiration (230) of the CCI, the IMD 10 will perform (240) the conduction check and determine if intrinsic conduction (250) is present. If intrinsic conduction is present, then the IMD 10 will operate in the atrial based pacing mode (260).

If intrinsic conduction is not found (250), then the CCI is increased by some predetermined amount (270). The CCI is evaluated (280) and if it is less than or equal to a maximum value then the process returns to the initiation of the CCI (220). This will either be at the maximum value of the CCI or at the increased value of the CCI (270). In this manner, the CCI is progressively increased until a maximum value is reached. That is, if the CCI is greater than the maximum value (280) the CCI is changed to the maximum value (290) and the process returns to (220). The amount of any given increase will be determined by the programmed pattern. As indicated, this may be 1, 2, 4, 8, 16, and 32 minutes and then 1, 2, 4, 8 and 16 hours with 16 hours being the maximum, in one embodiment. It should be appreciated that this progression is merely exemplary and more or fewer iterations may be utilized and values may be chosen accordingly. Furthermore, step (280) may be modified to include a counter such that multiple attempts may be made at a given value before increasing that value.

Figure 11:
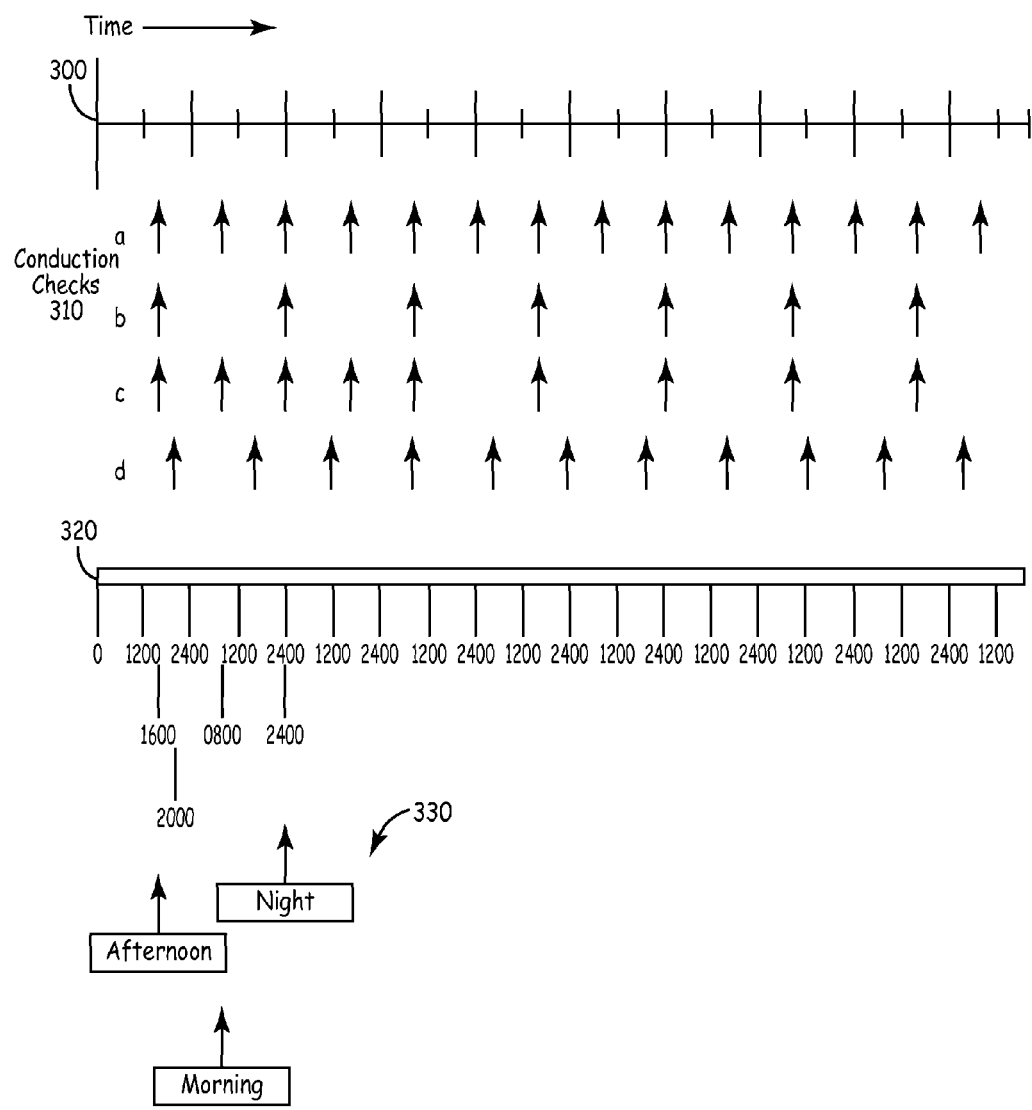
FIG. 11 is a schematic timing diagram indicative of conduction checks occurring on a periodic basis.

FIG. 11 is a schematic timing diagram indicative of conduction checks occurring on a periodic basis. Bars 300 and 320 both indicate time, with 12 hour intervals specifically indicated. Arrows 310 indicates the pattern of conduction checks occurring at maximum values. In pattern "a" conduction check are occurring every 16 hours. Referring to time bar 320 and time of day indicator 330, it is readily apparent that the first conduction check occurs 1600 hours, which is in the afternoon. The next conduction check will occur at 0800 hours, which is in the morning and the following conduction check occurs at 2400 hours (Midnight), which represents a nighttime evaluation. If a 16-hour interval is maintained, this pattern will repeat and circadian differentiation is achieved. It should be appreciated that the loss of conduction is the initiating event and the actual times of the day eventually utilized will follow from this triggering event.

Though not separately illustrated, this variation may be modified slightly to achieve further circadian variability. As indicated, with a 16 hour interval, the afternoon, morning, night progression will repeat, with conduction checks occurring at generally the same time (e.g., 1600, 0800, 2400). This set of conduction checks may be labeled as a complete circadian subset; that is, at least one check occurs during each of the three main daily time periods. After one circadian subset (or some predetermined number of subsets) an offset value may be introduced. The value chosen for the offset is not critical; one, two or three hours are exemplary, but any value (positive or negative) is acceptable. Thus, after the completion of the circadian subset (or the last in a predetermined number of circadian subsets), the offset value is added to the CCI value for one iteration. Thus, in the present example, the CCI maximum is sixteen hours; after one circadian subset, an offset value of one hour is added such that the next conduction check occurs 17 hours later, rather than 16. However, the offset value is not maintained and the subsequent conduction check occurs 16 hours later. Thus, an exemplary pattern might be 16-16-16-17-16-16, etc. Stated in another way, the conduction checks may occur at 1600 hours, 0800, hours, 2400 hours, 1700 hours, 0900, etc. In this manner, the circadian differentiation is always maintained between each subsequent conduction check and over time, further variation is imparted within each daily time period.

A feedback mechanism may be employed wherein successful conduction checks are noted and the offset value may be employed to cause the conduction checks to occur during periods of time shown to be successful in the past. In other words, the IMD 10 may learn patient specific parameters that increase the likelihood of a successful conduction check and tailor the progression accordingly.

Returning to FIG. 11, pattern "b" illustrates conduction checks occurring at 32 hour intervals. This maintains circadian variability, but with a longer interval more time elapses between subsequent conduction check but also between repetitive checking during any given time of day. Pattern "c" represents using a 16 hour interval for a period of time, and if unsuccessful increasing the maximum to 32 hours. While the number is non-limiting, conceptually if conduction checks continue to fail over a long period of time, the likelihood of success is lowered and less frequent conduction checks may be justified. Pattern "d" illustrates conduction checks occurring at a 20-hour interval. Thus, it is apparent that there are a variety of patterns that may be employed to achieve the desired temporal relationships.

In one embodiment, the algorithm used to search for intact AV conduction and restore ADI/R is defined according to one of two options. The first option is to simply withhold a ventricular pace stimulation during DDD/R operation (110). In the event that a ventricular sense (112) follows the physiologic atrial event during which ventricular pacing was withheld (110), ADI/R pacing is resumed. Otherwise, DDD/R pacing continues (114) with subsequent reattempts according to a schedule or by way of manual activation (as specified above). The second option searches for intact AV conduction involves extending the AV delay (110) during DDD/R pacing to a pre-designated AV conduction interval (AVCI). For instance, with an AVCI of 400 ms, the AV delay is extended to 400 ms following a physiologic atrial event (sensed or paced). In the event that the AV interval is interrupted by a ventricular sense, thereby preempting the ventricular pace in DDD/R operation, the mode supervisor (100) reverts to ADI/R operation. Otherwise, a ventricular pace is delivered upon the expiration of the AVCI interval and DDD/R operation resumes with reattempts according to the schedule (or with manual activation) as described above.

The mode supervisor monitors for repeated failed AV conduction tests at maximal test duration in one embodiment. So for example, if seven straight tests for AV conduction fail at 16-hour intervals, the mode supervisor can suspend AV conduction testing and the device can then remain in the DDD/R mode indefinitely. Alternatively, the present invention may continue to perform the conduction checks at the maximum interval. This allows for simple programming options. That is, even with complete heart block, the protocol operates beneficially to the patient and even if unlikely, a return of intrinsic conduction can be identified.

The present invention may be implemented using executable software code and/or operational parameters saved by (or downloaded to) a medical device. Such a device may be disposed in vivo and later programmed according to the invention or may be programmed prior to implantation (e.g., using firmware that may be reprogrammed or modified using telemetry techniques and the like). This is in contrast to a beat-to-beat implementation of the invention, which would preferably be implemented in hardware as understood by those of skill in the art. However, the present invention is not limited to only firmware or hardware implementations; indeed, the present invention may be implemented in a hybrid or combined in any desirable manner using device programming techniques known and used in the art.

It is to be understood that the above description is intended to be illustrative and, not restrictive. Many other embodiments will be apparent to those of skill in the art upon reading and understanding the above description. The scope of the invention should, therefore, be determined with reference to the appended claims, along with the full scope of equivalents to which such claims are

The invention claimed is:

1. An implantable medical device (IMD) comprising:
a processing unit for controlling the IMD and including a ventricular pacing protocol (VPP) module for selectively operating the IMD in an atrial based pacing mode or a dual chamber based pacing mode, wherein the VPP is a pacing protocol that tolerates a complete cardiac cycle devoid of ventricular activity while providing ventricular pacing in the cycle immediately subsequent to the cardiac cycle devoid of ventricular activity;
a pulse generator for selectively providing cardiac pacing under the control of the processing unit;
an intrinsic conduction checking module communicatively coupled with the processing unit and causing the processing unit to perform conduction checks when operating in the dual chamber based pacing mode, the conduction checks occurring according to a predetermined pattern.

2. The IMD of claim 1, wherein the pattern includes a minimum interval having a minimum duration between subsequent conduction checks and a maximum interval having a maximum duration between subsequent unsuccessful conduction checks.

3. The IMD of claim 2, wherein the intrinsic conduction checking module increases a duration of the interval between subsequent unsuccessful conduction checks until the maximum interval is reached.

4. The IMD of claim 3, wherein the intrinsic conduction checking module includes a maximum interval and performs conduction checks repeatedly at the maximum interval.

5. The IMD of claim of claim 4, wherein the intrinsic conduction checking module adds an offset value after a predetermined number of consecutive unsuccessful conduction checks performed at the maximum value.

6. The IMD of claim 5, wherein the predetermined number is three.

7. The IMD of claim 4, wherein the maximum duration has a value that provides circadian variation between subsequent unsuccessful conduction checks performed at the maximum interval.

8. The IMD of claim of claim 7, wherein the intrinsic conduction checking module adds an offset value after a predetermined number of consecutive unsuccessful conduction checks performed at the maximum value.

9. The IMD of claim 8, wherein the predetermined number is three.

10. The IMD of claim 4, wherein the maximum duration has a value that provides circadian variation between any three consecutive unsuccessful conduction checks performed at the maximum interval.

11. The IMD of claim of claim 10, wherein the intrinsic conduction checking module adds an offset value after a predetermined number of consecutive unsuccessful conduction checks performed at the maximum value.

12. The IMD of claim 3, wherein the duration is doubled after each unsuccessful conduction check until the maximum duration is reached.

13. The IMD of claim 1, wherein the cardiac cycle is defined by an A-A interval.

14. A method comprising:
   operating an implantable medical device having cardiac pacing capabilities in an atrial based pacing mode if intrinsic conduction is present and in a dual chamber pacing mode according to a ventricular pacing protocol (VPP) if intrinsic conduction is not present, wherein the VPP is a pacing protocol that tolerates a complete cardiac cycle devoid of ventricular activity while providing ventricular pacing in the cycle immediately subsequent to the cardiac cycle devoid of ventricular activity;
   performing a conduction check at predetermined intervals while operating in the dual chamber pacing mode, wherein the predetermined intervals vary according to a predetermined pattern provided for sequential unsuccessful conduction checks and the predetermined pattern includes an initial minimum interval and a maximum interval; and
   selecting a subsequent interval from the predetermined pattern with each unsuccessful conduction check, until the maximum interval is reached.

15. The method of claim 14, wherein the predetermined pattern includes doubling duration of the interval with each subsequent unsuccessful conduction check.

16. The method of claim 14, wherein the maximum interval is a value that provides for circadian differentiation between consecutive conduction checks performed at the maximum value.

17. The method of claim 14, wherein the maximum interval is a value that provides for circadian differentiation between any three consecutive unsuccessful conduction checks performed at the maximum value.

18. The method of claim 14, wherein the predetermined pattern 1 minute, 2 minutes, 4, minutes, 8 minutes, 16 minutes, 32 minutes, 1 hour, 2 hours, 4 hours, 8 hours and 16 hours respectively with the maximum interval being 16 hours.

19. The method of claim 14, further comprising adding an offset value to the maximum interval after a set of unsuccessful conduction checks have occurred at the maximum value.

20. The method of claim 19, wherein the set includes three consecutive unsuccessful conduction checks at the maximum value.

21. The method of claim 14, wherein the cardiac cycle is defined by an A-A interval.

* * * * *